United States Patent [19]

Seiler et al.

[11] 4,410,519

[45] Oct. 18, 1983

[54] TETRALINE DERIVATIVES, THEIR PRODUCTION AND PHARMACEUTICAL COMPOSITIONS CONTAINING THEM

[75] Inventors: Max P. Seiler, Basel; Andre Stoll, Birsfelden, both of Switzerland

[73] Assignee: Sandoz Ltd., Basel, Switzerland

[21] Appl. No.: 243,267

[22] Filed: Mar. 12, 1981

Related U.S. Application Data

[63] Continuation-in-part of Ser. No. 186,878, Sep. 12, 1980, abandoned.

[30] Foreign Application Priority Data

Sep. 14, 1979 [CH] Switzerland .................. 8347/79
Jul. 18, 1980 [CH] Switzerland .................. 5547/80

[51] Int. Cl.$^3$ ................ A61K 31/655; A61K 31/275; C07C 121/60; C07C 117/00
[52] U.S. Cl. ................ 424/226; 260/349; 260/404.5; 260/465 D; 260/465 E; 560/27; 560/43; 560/59; 560/61; 560/133; 560/250; 560/255; 564/56; 564/86; 564/167; 564/428; 424/300; 424/304; 424/309; 424/311; 424/312; 424/321; 424/322; 424/324; 424/330
[58] Field of Search ............ 260/465 D, 465 E, 349; 424/304, 226

[56] References Cited

U.S. PATENT DOCUMENTS

| | | | |
|---|---|---|---|
| 3,296,249 | 1/1967 | Bell | 424/244 |
| 3,991,207 | 11/1976 | Sarges et al. | 564/428 X |
| 4,010,202 | 3/1977 | Sugihara et al. | 564/374 X |
| 4,035,512 | 7/1977 | Sugihara et al. | 564/374 X |
| 4,057,582 | 11/1977 | Dunnigan et al. | 564/428 |

FOREIGN PATENT DOCUMENTS

2333847 1/1974 Fed. Rep. of Germany .
2752659 6/1978 Fed. Rep. of Germany .

OTHER PUBLICATIONS

McDermed, et al., Journal of Medicinal Chemistry, (1975), vol. 18, pp. 362–367.
McDermed, et al., Journal of Medicinal Chemistry, (1976), vol. 19, pp. 547–549.
Hacksell, et al., Journal of Medicinal Chemistry, (1979), vol. 22, pp. 1469–1475.

*Primary Examiner*—Joseph Paul Brust
*Attorney, Agent, or Firm*—Gerald D. Sharkin; Robert S. Honor; Thomas O. McGovern

[57] ABSTRACT

An optically active or racemic 2-amino-5-hydroxy-1,2,3,4-tetrahydronaphthalene wherein the nitrogen atom of the amino group carrier two alkyl groups, one of which is unsubstituted and the other is substituted by at least one functional group, or a physiologically hydrolysable ester thereof in free base form or in the form of an acid addition salt thereof is provided which is active against heart circulatory disorders and Morbus Parkinson and inhibits prolactin secretion inhibition.

18 Claims, No Drawings

TETRALINE DERIVATIVES, THEIR PRODUCTION AND PHARMACEUTICAL COMPOSITIONS CONTAINING THEM

This is a continuation-in-part of our application Ser. No. 186,878 filed Sept. 12, 1980 now abandoned.

This invention relates to new tetraline derivatives, their production and pharmaceutical compositions containing them.

German Offenlegungsschrift No. 2333847 discloses a very broad class of tetrahydronaphthols which are stated to be useful as water softeners, agents inhibiting the corrosivity of engine lubricants, as central nervous system depressants, as agents for the treatment of heart fibrillatory disorders, and of cardiac arrhythmia in warm blooded animals, as agents for lowering blood pressure and as disinfectants. These tetrahydronaphthols may bear a wide variety of substituents in the aromatic moiety and in the saturated ring moiety. The hydroxy group in the aromatic moiety may be in free form or be esterified. The saturated ring may bear an non-cyclic disubstituted amino group. The following substituents of such an amino group are named: alkyl; alkenyl; hydroxyalkyl and phenylalkyl. The only asymmetrically disubstituted amino group named and exemplified is the N-methyl-N-benzylamino group.

We have now surprisingly found that certain tetrahydronaphthols which are not specifically suggested or disclosed by the above-mentioned Offelegungsschrift possess notable pharmacological properties.

The present invention provides accordingly an 2-amino-5-hydroxy-1,2,3,4-tetrahydronaphthalene wherein the nitrogen atom of the amino group carries two alkyl groups, one of which is unsubstituted and the other is substituted by at least one functional group, or a physiologically hydrolysable ester thereof hereinafter referred to as a compound of the invention.

The compounds may have further substituents in other ring positions, preferably in the aromatic ring.

By the term functional group is covered groups classed in organic chemistry as reactive groups, including halogen atoms and unsaturated C—C groups, but excluding aromatic rings. It is to be appreciated that the functional group is attached directly to the alkyl chain and not through an aromatic ring.

In particular the invention provides compounds of formula I

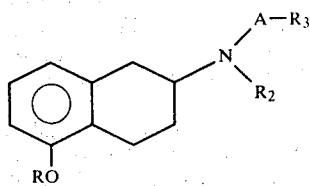

wherein
R is hydrogen or a group $R_1CO$ wherein $R_1CO$ is a pharmaceutically acceptable acyl moiety splittable off by hydrolysis under physiologically conditions,
$R_2$ is alkyl of 1 to 4 carbon atoms,
A is alkylene of 1 to 5 carbon atoms,
$R_3$ is halogen, a free or pharmaceutically acceptable esterified hydroxy group, SH, $N_3$, CN, $COR_4$, —NH—X—$R_5$, —Y—Alkyl of 1 to 4 carbon atoms, —Y—(Phenylalkyl) of 7 to 10 carbon atoms, —Y—Phenyl, or alkenyl or alkinyl of 2 to 4 carbon atoms,
$R_4$ is alkoxy of 1 to 4 carbon atoms or $NR_6R_7$,
$R_5$ is alkoxy of 1 to 4 carbon atoms, alkyl of 1 to 3 carbon atoms, $NR_6R_7$, phenyl unsubstituted or mono- or di-substituted, independently, by alkyl of 1 to 4 carbon atoms, alkoxy of 1 to 4 carbon atoms, fluorine, chlorine or bromine,
$R_6$ and $R_7$ are, independently, hydrogen or alkyl of 1 to 4 carbon atoms,
X is CO or $SO_2$ and
Y is O, S; SO or $SO_2$, with the proviso that when $R_5$ is alkoxy then X is CO.

The compounds of the invention may exist in the form of individual optical isomers, or in the form of racemates or in certain instances, e.g. when in formula I Y is —SO—, also in the form of diastereoisomers. Preferred are the compounds which have the same absolute configuration as Example 23 hereinafter.

A may be an unbranched or a branched alkylene chain. Preferably A is a —$(CH_2)_n$— chain wherein n is 1 to 5 or preferably 2 to 4. Most preferably n is 3.

$R_1$ is conveniently hydrogen, alkyl of from 1 to 19 carbon atoms, phenylalkyl of from 7 to 10 carbon atoms, or phenyl unsubstituted or mono- or di-substituted, independently, by alkyl of 1 to 4 carbon atoms, alkoxy of 1 to 4 carbon atoms, fluorine, chlorine or bromine.

$R_2$ is preferably n-propyl.

$R_3$ is preferably CN, S-alkyl of 1 to 4 carbon atoms, $NHSO_2NR_6R_7$, OH or fluorine.

When $R_3$ is an esterified hydroxy group, the ester may be derived from an acid of formula $R_1COOH$ or a carbamic acid which is unsubstituted on the nitrogen atom or bears one or two alkyl substituents of 1 to 10 carbon atoms.

One group of compounds comprises the compounds of formula Ia

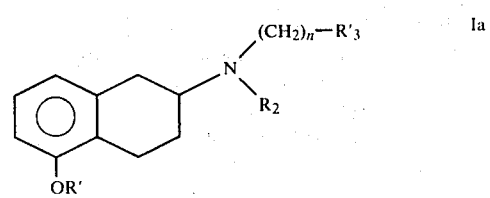

wherein
R' is hydrogen or a group $R_1'$ CO wherein $R_1$ is hydrogen, alkyl of 1 to 19 carbon atoms, phenylalkyl of 7 to 10 carbon atoms, or phenyl unsubstituted or mono- or di-substituted, independently, by alkyl of 1 to 4 carbon atoms, alkoxy of 1 to 4 carbon atoms, alkoxy of 1 to 4 carbon atoms, fluorine, chlorine or bromine,
$R_2$ is alkyl of 1 to 4 carbon atoms,
$R_3'$ is CN, $COR_4$, —NH—X—$NR_6R_7$ or —NH-$COR_5'$
$R_4$ is alkoxy of 1 to 4 carbon atoms or $NR_6R_7$,
$R_5'$ is alkyl of 1 to 3 carbon atoms,
X is CO or $SO_2$, and
n is a whole number from 2 to 5.

Another group of compounds comprises the compounds of formula Ib

[Structure Ib: tetrahydronaphthalene with N(A-R3)(R2) at 2-position and R'O at 5-position]

wherein
R' and R2 as defined above with respect to formula Ia,
A is alkylene of 1 to 5 carbon atoms,
R3 is halogen, a free or esterified hydroxy group, SH, N3, CN, —COR4, —NH—X—R5, —Y—alkyl of 1 to 4 carbon atoms, —Y—(Phenylalkyl) of 7 to 10 carbon atoms, —Y—phenyl, or alkenyl or alkinyl of 2 to 4 carbon atoms,
R4 is alkoxy of 1 to 4 carbon atoms or NR6R7,
R5 is alkoxy of 1 to 4 carbon atoms, alkyl of 1 to 3 carbon atoms, NR6R7, phenyl unsubstituted or mono- or di-substituted by alkyl of 1 to 4 carbon atoms, alkoxy of 1 to 4 carbon atoms, fluorine, chlorine or bromine,
R6 and R7 are, independently, hydrogen or alkyl of 1 to 4 carbon atoms,
X is CO or SO2, and
Y is O, S, SO or SO2,
with the proviso that (i) when R5 is alkoxy then X is CO and (ii) when A is —(CH2)$_{n'}$—, wherein n' is 2 to 5, then R3 is other than CN, COR4, NH—X—NR6R7, or NHCOR5' wherein R5' is alkyl of 1 to 3 carbon atoms.

The present invention provides additionally a process for the production of a compound of the invention which comprises a process for the production of a compound of the invention which comprises, for the production of a compound wherein the 5-hydroxy group is in free form, (a) introducing a functionally substituted alkyl group into an appropriate 2-mono-alkylamino-5-hydroxy-1,2,3,4-tetrahydronaphthalene, or (b) deprotecting a corresponding 2-dialkylamino-5-hydroxy-1,2,3,4-tetrahydronaphthalene which bears at least one functional group on one of the alkyl groups attached to the nitrogen atom, and wherein the hydroxy group is protected by a protecting group, or for the production of a compound wherein the 5-hydroxy group is esterified, (c) esterifying a corresponding compound of claim 1 wherein the 5-hydroxy group is in free form with an acid splittable off by hydrolysis under physiological conditions or a reactive derivative thereof.

In particular a compound of formula I may be produced by a process which comprises, for the production of a compound of formula I wherein R is hydrogen, (a) introducing a group R3—A— into a compound of formula II

[Structure II: tetrahydronaphthalene with NHR2 at 2-position and OH at 5-position]

wherein R2 is as defined above, or
(b) splitting off the group R8 from a compound of formula IV

[Structure IV: tetrahydronaphthalene with N(A-R3)(R2) at 2-position and OR8 at 5-position]

wherein
A, R2 and R3 are as defined above, and
R8 is a hydroxy protecting group, or
for the production of compounds of formula I wherein R is R1CO, (c) esterifying a compound of formula I wherein R1 is hydrogen.

Free base forms of the compounds of the invention may be converted into the acid addition salt forms in conventional manner and vice versa. Suitable acids for salt formation include inorganic acids such as hydrochloric acid or organic acids such as fumaric acid, malonic acid, pamoic acid, naphthalene-1,5-disulphonic acid, maleic acid etc.

Process (a) may be effected in conventional manner for the production of tertiary amines. Preferably the reaction is effected by using a compound of formula III $$R_3—A—Z$$

wherein Z is a leaving group, preferably chlorine, bromine, iodine, alkylsulphonyloxy or arylsulphonyloxy. Preferably the compounds of formula II and III are heated in an inert solvent such as dimethylformamide. The reaction may be effected in the presence of a base, e.g. a tertiary amine or an alkali metal carbonate or bicarbonate.

Process (b) may be effected in conventional manner for the splitting off of a hydroxy protecting group. R8 preferably is a lower alkyl group, especially methyl, an arylalkyl group, essentially benzyl, or an acyl group especially acetyl.

For the splitting off of an alkyl group, preferably a lewis acid in an inert organic solvent or an alkali metal alkyl mercaptide in an inert polar organic solvent is used. To split off an acyl group the compound of formula II is preferably warmed with an alcoholic hydrohalic acid.

The acylation process, process (c), may be effected in conventional manner for the acylation of a phenol. A suitable reactive acid derivative of a carboxylic acid is, for example, an acid halide or acid anhydride. The reaction is conveniently effected in an acidic solvent, e.g. trifluoroacetic acid, or in the presence of a base, e.g. pyridine.

For the production of certain compounds of formula I, e.g. compounds of formula I wherein one of the radicals RO and R3 is a free hydroxy group and the other is an esterified hydroxy group, selective reaction conditions may be chosen or temporary protecting groups may be used.

All the above reactions may be conveniently effected at temperatures from about 20° C. to about 200° C.

The compounds of the invention may be isolated and purified in known manner.

Optically active compounds of the invention may be produced from optically active starting materials (produced according to known methods for the splitting of racemate, see e.g. Example 23). Separation of optical isomers and diastereoisomers may also be effected with mixtures.

The starting materials, e.g. the compounds of formulae II and IV, are either known or may be produced in known manner or analogously to the methods described herein.

The compounds of formula IV may be produced, for example, in analogous manner to process (a) or by interconverting one radical $R_3$ of a compound of formula IV into another radical $R_3$, e.g. by replacing a halogen atom by an S-alkyl group with an alkylthiol or by oxidizing a S-alkyl moiety to form a $SO_2$alkyl or SO alkyl group using hydrogen peroxide or sodium periodate respectively.

In the following examples all the temperatures are in Celsius and are uncorrected. In the following N.M.R. spectra S = singlet, M = multiplet and T = triplet. Propyl is n-propyl.

The Example 23 compound is the preferred compound.

EXAMPLE 1:
2-[N-(4-cyanobutyl)-N-propylamino]-1,2,3,4-tetrahydro-5-hydroxy-naphthalene (process a)

4 g 2-N-propylamino-1,2,3,4-tetrahydro-5-hydroxynaphthalene in 100 ml dimethylformamide are treated with 3.8 ml N-ethyl-N,N-disopropylamine and then with 2.5 g 5-bromovaleric acid nitrile. The mixture is stirred for 2 days at 60° and finally the solvent removed therefrom in a high vacuum. The residue is extracted with aqueous 1 N sodium bicarbonate solution/methylene chloride. The organic phase is dried over sodium sulphate, concentrated and the residue is chromatographed in silicagel using an eluant methylene chloride (saturated with ammonia to an extent of about 10%)/methanol 95:5.

The title compound is obtained as an amorphous solid which is converted into the crystalline hydrochloride. M.pt. 156°-158° (methanol/ether).

EXAMPLE 2:
1,2,3,4-tetrahydro-5-hydroxy-2-[N-(3-methylthiopropyl)-N-propylamino]naphthalene (process b)

1 g sodium hydride in 40 g dimethylformamide is treated at 0° with 3.3 ml ethylmercaptan. 4.5 g 1,2,3,4-tetrahydro-5-methoxy-2-[N-(3-methylthiopropyl)-N-propylamino]-naphthalene in 30 ml dimethylformamide are added. The reaction mixture is stirred for 20 hours at 120°, cooled, concentrated and partitioned between ether and 2 N hydrochloric acid. The aqueous phase is adjusted to pH 11 at 5° and extracted with methylene chloride. The organic phase is dried, filtered and concentrated to give the crude title compound, which is converted into the hydrogen fumarate in isopropanol/pentane. M.pt. sintering from 70° (from ethanol/ether). The starting material may be obtained as follows:

(a) 1,2,3,4-tetrahydro-2-[N-(3-hydroxypropyl)-N-propylamino]-5-methoxynaphthalene 185.4 g 1,2,3,4-tetrahydro-5-methoxy-2-(propylamino)naphthalene, 263.2 g 3-iodopropanol, 350.3 g potassium carbonate and 2 liters acetone are refluxed with stirring for 20 hours.

35.8 g 3-iodopropanol are added and the mixture refluxed for a further 8 hours. The mixture is filtered and concentrated. The residue is partitioned between 1 N sodium thiosulphate and methylene chloride. The organic phase is dried over sodium sulphate and concentrated to give the heading compound in crude form which is converted into the bis[base]naphthalene-1,5-disulphonate. M.pt. 99°-101° (decomp).

(b) 2-[N-(3-chloropropyl)-N-propylamino]-1,2,3,4-tetrahydro-5-methoxy-naphthalene 185.8 g thionylchloride are added to 190 g 1,2,3,4-tetrahydro-2-[N-(3-hydroxypropyl)-N-propylamino]-5-methoxy-naphthalene (free base) in 1.5 liters chloroform. The resultant warm reaction mixture is refluxed for 1 hour, and after concentration partitioned between methylene chloride and 2 N sodium hydroxide. The organic phase is washed with water, dried over sodium sulphate, filtered and concentrated. The crude heading compound so obtained is converted into the bis[base]-naphthalene-1,5-disulphonate. M.pt. 239°-242° (decomp).

(c) 1,2,3,4-tetrahydro-5-methoxy-2-[N-(3-methylthiopropyl)-N-propylamino]naphthalene 2.35 g sodium are dissolved in 50 ml absolute ethanol and immediately 4.8 g methylmercaptan in 60 ml ethanol are added dropwise. The mixture is warmed to 45° and at this temperature a solution of 19.7 g 2-[N-(3-chloropropyl)-N-propylamino]-1,2,3,4-tetrahydro-5-methoxynaphthalene in 120 ml absolute ethanol are added. The mixture is stirred at 50° for 1 hour. The residue is partitioned between ether and water. The ether phase is dried over potassium carbonate, filtered and concentrated. The resultant oil containing the heading compound is used further as such.

In analogous manner to Examples 1 and 2 the following compounds of formula I are obtained wherein R is H and A is $(CH_2)_n$:

| EXAMPLE | $R_2$ | n | $R_3$ | Salt form | M. pt. |
|---|---|---|---|---|---|
| 3 | $C_3H_7$[6] | 3 | CN | HCl | 194–197° |
| 4 | $C_3H_7$ | 2 | $NHSO_2N(C_2H_5)_2$ | HCl | 220° |
| 5 | $C_2H_5$ | 3 | CN | HCl | 237–239° |
| 6 | $C_2H_5$ | 3 | $COOCH_3$ | HCl | 160–163° |
| 7 | $C_3H_7$ | 2 | CN | HCl | 203° |
| 8 | $C_2H_5$ | 3 | $CONHCH_3$ | HCl | 179–182° |
| 9 | $C_3H_7$ | 3 | $OCH_3$ | (Base) | 127–128.5° |
| 10 | $C_3H_7$ | 3 | OH | (Base) | 129–130.5° |
| 11 | $C_3H_7$ | 3 | F | HCl | 171–174° |
| 12 | $C_3H_7$ | 3 | $CH=CH_2$ | HCl | 148–151° |
| 13 | $C_3H_7$ | 3 | $N_3$ | HCl | 126–128° |
| 14 | $C_3H_7$ | 3 | $SO_2CH_3$ | HCl | 196–200° |
| 15 | $C_3H_7$ | 3 | $SOCH_3$ | (Base) | Oil[1] |
| 16 | $C_3H_7$ | 3 | Cl | Naphthalene-1,5-disulphonate[7] | 218–220° |
| 17 | $C_3H_7$ | 3 | $OOCNH_2$ | Naphthalene-1,5-disulphonate[7] | 156–161° |
| 18 | $C_3H_7$ | 3 | $OOCCH_3$ | (Base) | Oel[2] |
| 19 | $C_3H_7$ | 3 | $NHCOOC_2H_5$ | HCl | 123° (decomp) |

-continued

| EXAMPLE | $R_2$ | n | $R_3$ | Salt form | M. pt. |
|---|---|---|---|---|---|
| 20 | $C_3H_7$ | 3 | $COOCH_3$ | HCl | 159–161° |
| 21 | $C_3H_7$ | 3 | $NHCON(C_2H_5)_2$ | Hydrogen pamoate | 150° (decomp) |
| 22 | $C_3H_7$ | 3 | CN | HCl | 187–188°[3] |
| 23 | $C_3H_7$ | 3 | CN | HCl | 187–188°[4] |
| 24 | $C_3H_7$ | 3 | $NHCONHC(CH_3)_3$ | (Base) | Foam[5] |
| 25 | $C_3H_7$ | 3 | $NHSO_2NH_2$ | Fumarate | 203–205° (decomp) |
| 26 | $C_3H_7$ | 3 | $NHSO_2N(CH_3)_2$ | HCl | 161–163° (decomp) |
| 27 | $C_3H_7$ | 3 | $CONHCH_3$ | Naphthalene-1,5-disulphonate[7] | 226–229° |
| 28 | $C_3H_7$ | 3 | $NHCONH_2$ | Hydrogen fumarate | 80° (decomp) |
| 29 | $C_3H_7$ | 3 | $NHCOCH_3$ | (Base) | 117–118° |
| 30 | $CH_3$ | 3 | CN | Naphthalene-1,5-disulphonate[7] | 230–232° |
| 31 | $C_3H_7$ | 3 | $SCH_3$ | Hydrogen fumarate | 70° (decomp)[8] |
| 32 | $C_3H_7$ | 3 | $SCH_3$ | Hydrogen fumarate | 70° (decomp)[9] |

[1] NMR (CDCl$_3$) SOCH$_3$: 2.59δ(S) - CH$_2$—CH$_3$: 0.88δ(T)
[2] NMR (CDCl$_3$) SOCH$_3$: 4.13δ(T) - OOC—CH$_3$: 2.03δ(S)
[3] (+)-optical isomer of the compound of Example 3 $[\alpha]_D^{20} = +63°$, c = 2, (hydrochloride in Methanol)
[4] (−)-optical isomer of the compound of Example 3 $[\alpha]_D^{20} = -63°$, c = 2, (hydrochloride in Methanol)

The compound can be produced, e.g. as follows for process (a),:-

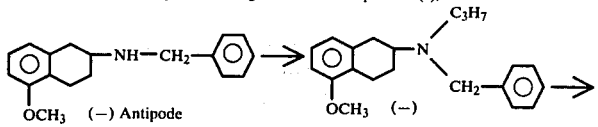
(J. Med. Chem. 19, 547, (1976))

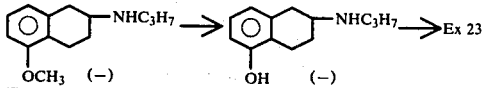

[5] NMR (CDCl$_3$) 3 aromat.H: 6.5–7.0δ(M), 2NH: 5.3–6.5δ(broad)
9 tert.Bu—H: 1.38δ(S), CH$_2$—CH$_3$: 0.88δ(T)
[6] In this table C$_3$H$_7$ is always n-C$_3$H$_7$.
This salt contains 2 moles base and 1 mole naphthalene-1,5-disulphonic acid.
[8] (+) optical isomer of compound of Example 2, $[\alpha]_D^{20} = +48.6°$ (hydrogen fumarate, c = 1 in methanol)
[9] (−) optical isomer of compound of Example 2, $[\alpha]_D^{20} = -48.6°$ (hydrogen fumarate, c = 1 in methanol)

EXAMPLE 33:
2-[N-ethyl-N-(3-methoxycarbonylpropyl)amino]-1,2,3,4-tetrahydro-5-acetoxynaphthalene (process c)

A stirred solution of 1.7 g 2-[N-ethyl-N-methoxycarbonylpropyl)amino]-1,2,3,4-tetrahydro-5-hydroxynaphthalene in 15 ml trifluoroacetic acid is treated dropwise with 1.5 ml acetyl bromide at room temperature. Thin layer chromatography after 1.5 hours indicates a practically quantitative conversion. The mixture is concentrated to dryness and the residue dried under a high vacuum and then partitioned between 1 N sodium carbonate/methylene chloride. The organic phase is dried, concentrated, taken up in a little acetone and treated with a saturated solution of fumaric acid in acetone. The hydrogen fumarate of the title compound is obtained from the concentrated acetone solution and after careful drying isolated as an amorphous foam.

In analogous manner to Example 33 the following compound of formula I is obtained.

EXAMPLE 34
R=CH$_3$CO; R$_2$=n—C$_3$H$_7$; A=(CH$_2$)$_3$; R$_3$=CN
M.pt. of hydrogen malonate 128°–9°.

EXAMPLE 35
R=C$_6$H$_5$CO; R$_2$=n—C$_3$H$_7$; A=(CH$_2$)$_3$; R$_3$=CN

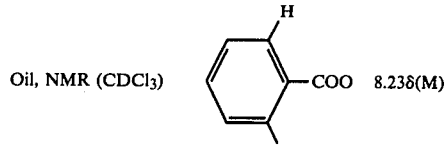

Oil, NMR (CDCl$_3$)

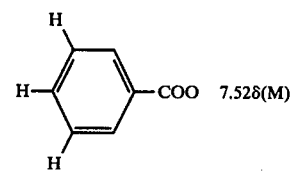

CH$_2$CN: 2.40 (T)
CCH$_3$: 0.90 (T)

The following compounds of formula I wherein A is —CH(CH$_3$)CH$_2$—CH$_2$—CH$_2$— and R$_2$ is ethyl may be obtained wherein:

| Ex | R | R$_3$ |
|---|---|---|
| (a) | H | SH |
| (b) | HCO | CONH$_2$ |
| (c) | nC$_{18}$H$_{37}$CO | CON(n-C$_4$H$_9$)$_2$ |
| (d) | C$_6$H$_5$CH$_2$CO | NHSO$_2$N(nC$_4$H$_9$)$_2$ |
| (e) | C$_6$H$_5$C$_4$H$_8$CO | NHSO$_2$nC$_3$H$_7$ |
| (f) | 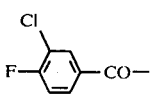 | 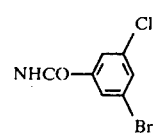 |

-continued

| Ex | R | $R_3$ |
|---|---|---|
| (g) | 3-Br, 2-$C_2H_5$-benzoyl (C6H3(Br)(C2H5)-CO-) | 2-F, 4-$C_2H_5O$-phenyl-NHSO2- |
| (h) | 4-$C_2H_5O$-C6H4-CO- | 4-$C_2H_5$-C6H4-NHSO2- |
| (i) | H | NH—CO—C6H5 |
| (j) | H | NH—CO—NH2 |
| (k) | H | $NHSO_2NH_2$ |
| (l) | $CH_3CO$ | O—$CH_2$—$C_6H_5$ or S—$CH_2$—$C_6H_5$ |
| (m) | H | SO—$(CH_2)_4$—$C_6H_5$ |
| (n) | H | $SO_2(CH_2)_4C_6H_5$ |
| (o) | H | $OC_6H_5$ |
| (p) | H | $SOC_6H_5$ |
| (q) | H | $SO_2C_6H_5$ |
| (r) | H | $SC_6H_5$ |
| (s) | H | C≡C—$CH_2CH_3$ |
| (t) | H | OOCH |
| (u) | H | $OOCC_{19}H_{39}$ |
| (v) | H | $OOCCH_2C_6H_5$ |
| (w) | H | $OOCC_4H_8C_6H_5$ |
| (x) | H | OOC-(3-Cl, 4-F-phenyl) |
| (y) | H | OOC-(4-Br, 2-$C_2H_5$-phenyl) |
| (z) | H | OOC-(4-$OC_2H_5$-phenyl) |

The compounds of the invention possess pharmacological activity and accordingly are useful as pharmaceuticals, e.g. for therapy.

In particular they stimulate dopamine receptors. For example they stimulate peripheral dopamine receptors, as indicated in standard animal tests, e.g. by a blood pressure lowering and a rise in the blood flow in the arteria mesenterica of the anaesthetized dog in doses of from about 0.1 to about 10 mg/kg i.v.

The compounds of the invention are therefore useful in the treatment of heart circulatory disorders, in particular treatment of hypertension, renal failure, congestive heart failure and heart insufficiency.

Additionally the compounds stimulate central dopamine receptors, as indicated in standard animal tests. In one standard test carried out according to the principles of U.Ungersted, Acta physiol. scand. Suppl. 367, 69–93, (1973) the nigro-neostriatalum dopamine pathway of rats is unilaterally destroyed by injection of 6-hydroxydopamine into the substantia nigra. The compounds are administered at doses of from about 0.3 to about 20 mg/kg i.p., and induced a rotation in the direction of the non-denerved side. The compounds also have a central dopaminergic effect as indicated by activity in the apomorphine stereotypy test at a dose of 30 mg/kg i.p.

The compounds are therefore additionally useful for the treatment of Morbus Parkinson.

The compounds additionally inhibit prolactin secretion as indicated by a lowering of the serum prolactin concentration of male rats, as determined by radioimmunoassay methods in conventional manner, when the rats are administered with from about 0.1 to about 10 mg/kg s.c., and the blood is obtained after decapitation of the animals.

The compounds are therefore additionally useful as prolactin secretion inhibitors, e.g. for the treatment of acromegaly.

For all the above uses the dosage will, of course, vary depending on the compound employed, mode of administration and treatment desired. However, in general, satisfactory results are obtained when administered at a daily dosage of from about 0.03 to about 20 mg per kg animal body weight (e.g. 0.03 to 5 mg/kg), conveniently given in divided doses 2 to 4 times a day or in sustained release form. For the larger mammals, the total daily dosage is in the range from about 2 to about 1000 mg (e.g. 2 to 100 mg), and dosage forms suitable for oral administration comprise from about 0.5 to about 500 mg (e.g. 0.5 to 50 mg) of the compounds admixed with a solid or liquid pharmaceutical carrier or diluent.

The compounds may be administered in pharmaceutically acceptable acid addition salt forms. These show the same order of activity as the free base forms. The present invention provides a compound of the invention in free base form or in pharmaceutically acceptable acid addition form in association with a pharmaceutical carrier or diluent. These pharmaceutical compositions may be formulated in conventional manner to be, for example, a solution or tablet.

The compounds of Examples 23 and 32 have particularly interesting activity and have been found to be active as anti-parkinson agents in the rat at a dose of 1 mg/kg i.p. with a duration of action of several hours.

In a first group of compounds $R_1$ is hydrogen.
In a 2nd group of compounds $R_1$ is alkyl.
In a 3rd group of compounds $R_1$ is phenalkyl.
In a 4th group of compounds $R_1$ is optionally substituted phenyl.
In a 5th group of compounds $R_3$ is halogen.
In a 6th group of compounds $R_3$ is OH.
In a 7th group of compounds $R_3$ is an esterified OH group.
In a 1st subgroup the ester is derived from a carbamic acid unsubstituted in the nitrogen atom.
In a 2nd subgroup the ester is derived from a carbamic acid substituted by alkyl.
In a 3rd subgroup the ester is derived from a carboxylic acid.
In an 8th group of compounds $R_3$ is SH.
In a 9th group of compounds $R_3$ is $N_3$.
In a 10th group of compounds $R_3$ is CN.
In an 11th group of compounds $R_3$ is $COR_4$.
In a 1st subgroup $R_4$ is alkoxy.
In a 2nd subgroup $R_4$ is $NR_6R_7$.
In a 12th group of compounds $R_3$ is —NH—X—$R_5$.
In a 1st subgroup X is CO.
In a 2nd subgroup X is $SO_2$.
In a 3rd subgroup $R_5$ is alkoxy.
In a 4th subgroup $R_5$ is alkyl.
In a 5th subgroup $R_5$ is $NR_6R_7$.
In a 6th subgroup $R_5$ is optionally substituted phenyl.
In a 13th group of compounds $R_3$ is Y alkyl.
In a 1st subgroup $R_3$ is O alkyl.

In a 2nd subgroup R$_3$ is S alkyl.
In a 3rd subgroup R$_3$ is SO alkyl.
In a 8th subgroup R$_3$ is SO$_2$alkyl.
In a 14th group of compounds R$_3$ is Y—(phenylalkyl).
In a 1st subgroup R$_3$ is O phenylalkyl.
In a 2nd subgroup R$_3$ is S phenylalkyl.
In a 3rd subgroup R$_3$ is SO phenylalkyl.
In a 4th subgroup R$_3$ is SO$_2$ phenylalkyl.
In a 15th group of compounds R$_3$ is alkenyl.
In a 16th group of compounds R$_3$ is alkinyl.

What we claim is:

1. An optically active or racemic compound of formula I

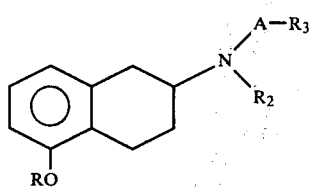

in which
R is hydrogen or a group R$_1$CO wherein R$_1$CO is a pharmaceutically acceptable acyl moiety which is hydrolysable under physiological conditions;
R$_2$ is alkyl of 1 to 4 carbon atoms;
A is alkylene of 1 to 5 carbon atoms, and
R$_3$ is CN or N$_3$
in free base form or the form of a pharmaceutically acceptable acid addition salt thereof.

2. A compound according to claim 1 in which R$_1$ is hydrogen, alkyl of 1 to 19 carbon atoms, phenylalkyl of 7 to 10 carbon atoms, or phenyl unsubstituted or mono- or di-substituted, independently, by alkyl of 1 to 4 carbon atoms, alkoxy of 1 to 4 carbon atoms, fluorine, chlorine or bromine.

3. A compound of claim 1 in which R$_3$ is CN.

4. A compound according to claim 1 in which A is —(CH$_2$)$_3$—.

5. A compound according to claim 1 in which R$_2$ is n-propyl.

6. The compound of claim 1 which is 2-[N-(3-cyano-propyl)-N-propylamino]-1,2,3,4-tetrahydro-5-hydoxynaphthalene in free base form or in the form of a pharmaceutically acceptable acid addition salt thereof.

7. The compound of claim 1 which is (−)2-[N-(3-cyano-propyl)-N-propylamino]-1,2,3,4-tetrahydro-5-hydroxynaphthalene in free base form or in the form of a pharmaceutically acceptable acid addition salt thereof.

8. The compound of claim 1 which is (+)2-[N-(3-cyano-propyl)-N-propylamino]-1,2,3,4-tetrahydro-5-hydroxynaphthalene in free base form or in the form of a pharmaceutically acceptable acid addition salt thereof.

9. The compound of claim 1 which is 2-[N-(4-cyano-butyl)-N-propylamino]-1,2,3,4-tetrahydro-5-hydroxynaphthalene in free base form in the the form of a pharmaceutically acceptable acid addition salt thereof.

10. The compound of claim 1 in which R is hydrogen and A is (CH$_2$)$_n$ and R$_2$, n and R$_3$ are C$_2$H$_5$, 3 and CN, respectively, in free base form or in the form of a pharmaceutically acceptable acid addition salt thereof.

11. The compound of claim 1 in which R is hydrogen and A is (CH$_2$)$_n$ and R$_2$, n and R$_3$ are C$_3$H$_7$, 2 and CN, respectively, in free base form or in the form of a pharmaceutically acceptable acid addition salt thereof.

12. The compound of claim 1 in which R is hydrogen and A is (CH$_2$)$_n$ and R$_2$, n and R$_3$ are C$_3$H$_7$, 3 and N$_3$, respectively, in free base form or in the form of a pharmaceutically acceptable acid addition salt thereof.

13. The compound of claim 1 in which R is hydrogen and A is (CH$_2$)$_n$ and R$_2$, n and R$_3$ are CH$_3$, 3 and CN, respectively, in free base form or in the form of a pharmaceutically acceptable acid addition salt thereof.

14. A pharmaceutical composition comprising a therapeutically effective amount of a compound of claim 1 in free base form or in pharmaceutically acceptable acid addition salt form in association with a pharmaceutical carrier or diluent.

15. A method of treating Morbus Parkinson which comprises administering a therapeutically effective amount of a compound of claim 1 to a subject in need of such treatment.

16. A method of treating heart circulatory disorders which comprises administering a therapeutically effective amount of a compound of claim 1 to a subject in need of such treatment.

17. A method of treating hypertension which comprises administering a therapeutically effective amount of a compound of claim 1 to a subject in need of such treatment.

18. A method of inhibiting prolactin secretion which comprises administering a therapeutically effective amount of a compound of claim 1 to a subject in need of such treatment.

* * * * *